United States Patent
Watson

(10) Patent No.: US 10,529,452 B2
(45) Date of Patent: Jan. 7, 2020

(54) COMPUTER MEMORY WITH IMPROVED PERFORMANCE THROUGH SINGLE-BIT LOGIC

(71) Applicant: ONICS LTD, Hornell, NY (US)

(72) Inventor: James Victor Watson, Great Shelford (GB)

(73) Assignee: ONICS LTD, West Drayton (GB)

( * ) Notice: Subject to any disclaimer, the term of this patent is extended or adjusted under 35 U.S.C. 154(b) by 0 days.

(21) Appl. No.: 16/201,929

(22) Filed: Nov. 27, 2018

(65) Prior Publication Data

US 2019/0333637 A1    Oct. 31, 2019

Related U.S. Application Data

(63) Continuation of application No. 13/106,766, filed on May 12, 2011, now abandoned.

(51) Int. Cl.
*G16H 50/20*    (2018.01)
*G06Q 10/10*    (2012.01)

(52) U.S. Cl.
CPC ............. *G16H 50/20* (2018.01); *G06Q 10/10* (2013.01)

(58) Field of Classification Search
None
See application file for complete search history.

(56) References Cited

U.S. PATENT DOCUMENTS

| | | | |
|---|---|---|---|
| 2002/0035486 A1* | 3/2002 | Huyn | G06F 19/3418 705/3 |
| 2004/0172294 A1* | 9/2004 | Dahlin | G06Q 10/0633 705/2 |
| 2010/0250271 A1* | 9/2010 | Pearce | G06Q 50/22 705/2 |

* cited by examiner

Primary Examiner — Michael Tomaszewski
(74) Attorney, Agent, or Firm — Knobbe, Martens, Olson & Bear, LLP

(57) ABSTRACT

Computer memory employs single-bit logic in order to improve performance through minimizing storage size for generating user interface prompts. The user interface prompts may be used to guide clinical or other decision queries using a dynamic decision tree such that multiple decision trees are followed in sequence and jumps occur between decision trees based on previously received query responses and the system's determination of what useful data has not been gathered. Throughout the process, the computer memory performs using highly efficient single-bit data storage and retrieval. For example, rather than storing data concerning all possible paths between various decision trees, a system using the computer memory may determine at the time of use that a jump should occur from one decision tree to another decision tree despite the system not being pre-populated with data representative of a relationship between the source and destination of the jump. Such jumps may be achieved without the use of complex data structures at the memory level, minimizing space usage and maximizing memory performance.

20 Claims, 14 Drawing Sheets

HISTORY OF PRESENT COMPLAINT — 601

This patient presented with symptoms and — 605 findings that suggested a primary left breast tumor. She complained of malaise, a lump in the breast, a lump in the axilla but not lethargy, weight loss, changes to the skin, change in shape or altered consistency. The non-specific general symptom of malaise had been noted for three months of less. The specific symptom of a lump in the breast had been noted for about four months. The specific symptom of a lump in the axilla had been noted for one month or less. The lump in the breast was in the upper outer quadrant. The primary lump had a size of 2.1 – 3.5cm. The tumor was irregular and hard, but was not indurated or inflammatory.

| 602 | 603 | 604 |
|---|---|---|
| Edit | Add Free Text | Continue → |

*Fig. 6.*

COMPUTER MEMORY WITH IMPROVED PERFORMANCE THROUGH SINGLE-BIT LOGIC

BACKGROUND

Many tasks require complex information acquisitions which include a series of information queries. Often, the information results obtained in response to one or more queries will affect what information queries subsequently occur. For example, a medical diagnosis may involve a physician reviewing a patient's past medical records, interviewing the patient for information about their history and present condition, conducting a physical examination, performing and/or order laboratory tests, biopsies, and other data inquiries. A medical diagnosis may be guided by certain standard inquiry sequences which are used according to established standards of care, billing guidelines, and/or other bases. Although skilled medical judgment remains central to a diagnosis, external tools and guidelines may increase efficiency, compliance with standards, and verifiability. As the use of computer-based technologies becomes increasingly common in medical practice, the need for more dynamic, efficient, and non-intrusive solutions increases.

Physicians increasingly are using electronic medical record systems ("EMR"). Notwithstanding this, the ability to capture quickly and easily a clinical note during a consultation remains a source of frustration as information overload, either consciously or subconsciously, may frequently be encountered. During a consultation the physician must socially engage with, and reassure, the patient whilst simultaneously making observations and/or requesting investigations relevant to the patient's condition. In an example of a cancer diagnosis, the physician may then consider the acquired data in order to arrive at a diagnosis. A treatment strategy may be created, involving surgery, chemotherapy and radiotherapy in any combination or permutation. In addition, each of these disciplines may require many factors to input into an effective decision making process.

Traditionally, the physician will make written notes that act as an "aids-de-memoire", before formalizing the annotations by dictating for a transcription secretary. Many EMR systems emulate this process by providing "fields" for the required clinical elements (e.g. history of present complaint/illness, review of systems, past histories, examination findings and investigation results such as imaging, biopsy and histology findings) into which the dictated notes are transcribed.

The addition of modern computer systems into the medical field with attendant EMR systems often require the physician to acquire several new skills including typing, use of the mouse and navigation through an application. Through requiring less of the physician's attention being spent on it, a clinical information acquisition system allows the physician to dedicate more attention to the patient.

BRIEF DESCRIPTION OF THE DRAWINGS

The accompanying drawings, which are incorporated in, and form, a part of this specification, illustrate example embodiments of the inventive subject matter, and in no way limit the scope of protection. The accompanying drawings include examples of graphical user interfaces for use with the disclosed system and methods. Other embodiments are contemplated using alternate hardware and/or software platforms, and using significantly different interfaces. The accompanying drawings illustrate embodiments wherein:

FIG. 6 illustrates an example user interface which provides natural language text describing stored clinical information.

DETAILED DESCRIPTION OF SPECIFIC EMBODIMENTS

Specific embodiments will now be described with reference to the drawings. These embodiments are intended to illustrate, and do not limit, the inventions set forth in the claims. Nothing in this detailed description is intended to imply that any particular feature, characteristic, or component of the disclosed systems, methods, and computer readable media is essential. Although the following description focuses on clinical applications, the disclosed decision forest system and methods can also be used for other (non-medical) applications involving decision trees. Examples of such other applications include business decision, risk assessment, and technical support problem resolution.

Overview

In one embodiment, a physician meets with a patient and uses a computer-based system involving a tablet computer in order to assist in gathering patient history information, determining the next courses of clinical action, making a diagnosis and writing a prescription. The clinical data acquisition system includes a dynamic decision forest which is used to provide efficient, adaptable guidance in the clinical steps performed. A dynamic decision forest may comprise a plurality of decision trees, at least some of which lack any predefined relationship. Despite this lack of predefined relationship amongst at least some trees, a dynamic decision forest may be capable of performing those decision trees in sequence based, for example, upon dynamically assessed data. For example, the system may maintain patient data concerning the particular patient. The system may initially populate the patient data, for example based on previous records stored within or accessible to the system. Alternatively or additionally, the system may begin without any data specific to the patient, and may prompt the physician to obtain such data by taking a guided medical history from the patient. For example, the system may provide user interface data to the physician user. The user interface data may relate to a user interface accessible on a device such as a touch-sensitive tablet computing device. In this embodiment, the system provides user interface data relating to a simple interface in which the physician is presented with a query and a series of possible responses, for example a question to ask the patient and a small number of possible responses. The responses may be selectable by the physician through touching the tablet device, and the responses entered for past queries may affect the later queries which the system presents to the physician.

Figure 1A:
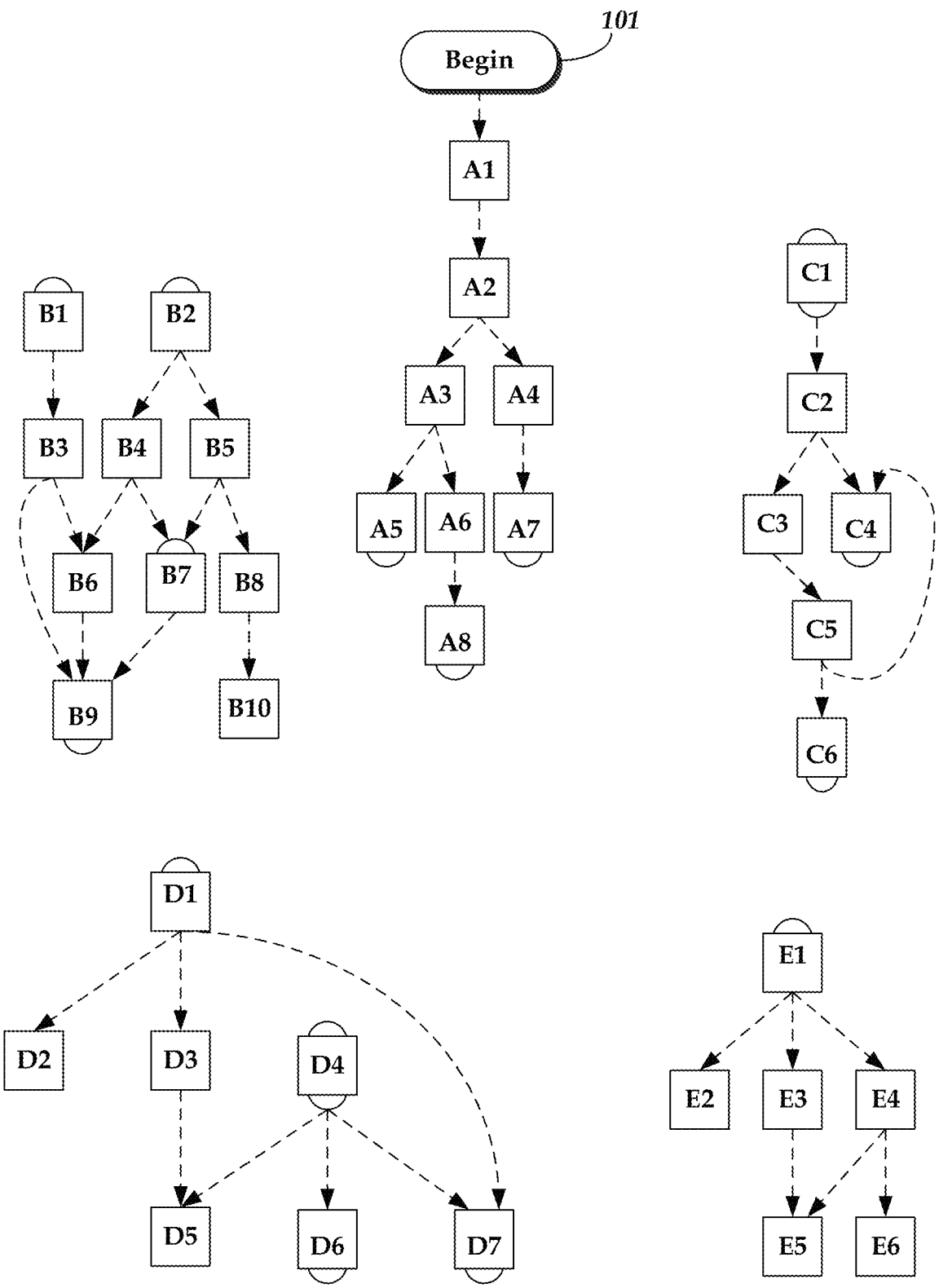
FIG. 1a is illustrative of an example dynamic decision forest in which decision nodes are connected to form decision trees and at least some decision trees lack a pre-defined sequence prior independent of an information acquisition occurrence.
Figure 1B:
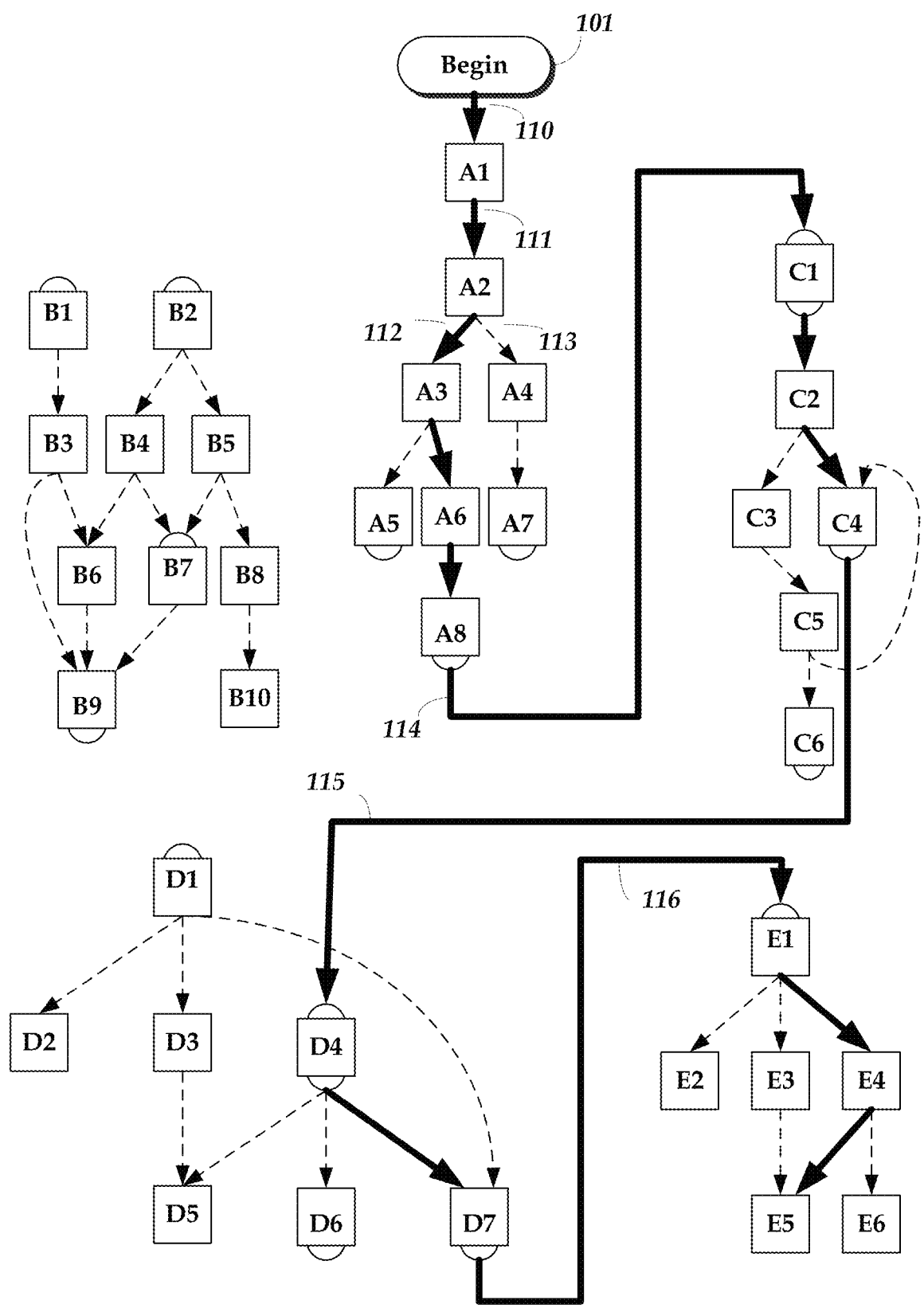
FIGS. 1b-1d are illustrative examples of use cases for a dynamic decision forest. Decision trees have been dynamically linked during an information acquisition to provide a dynamic decision pathway.
Figure 1C:
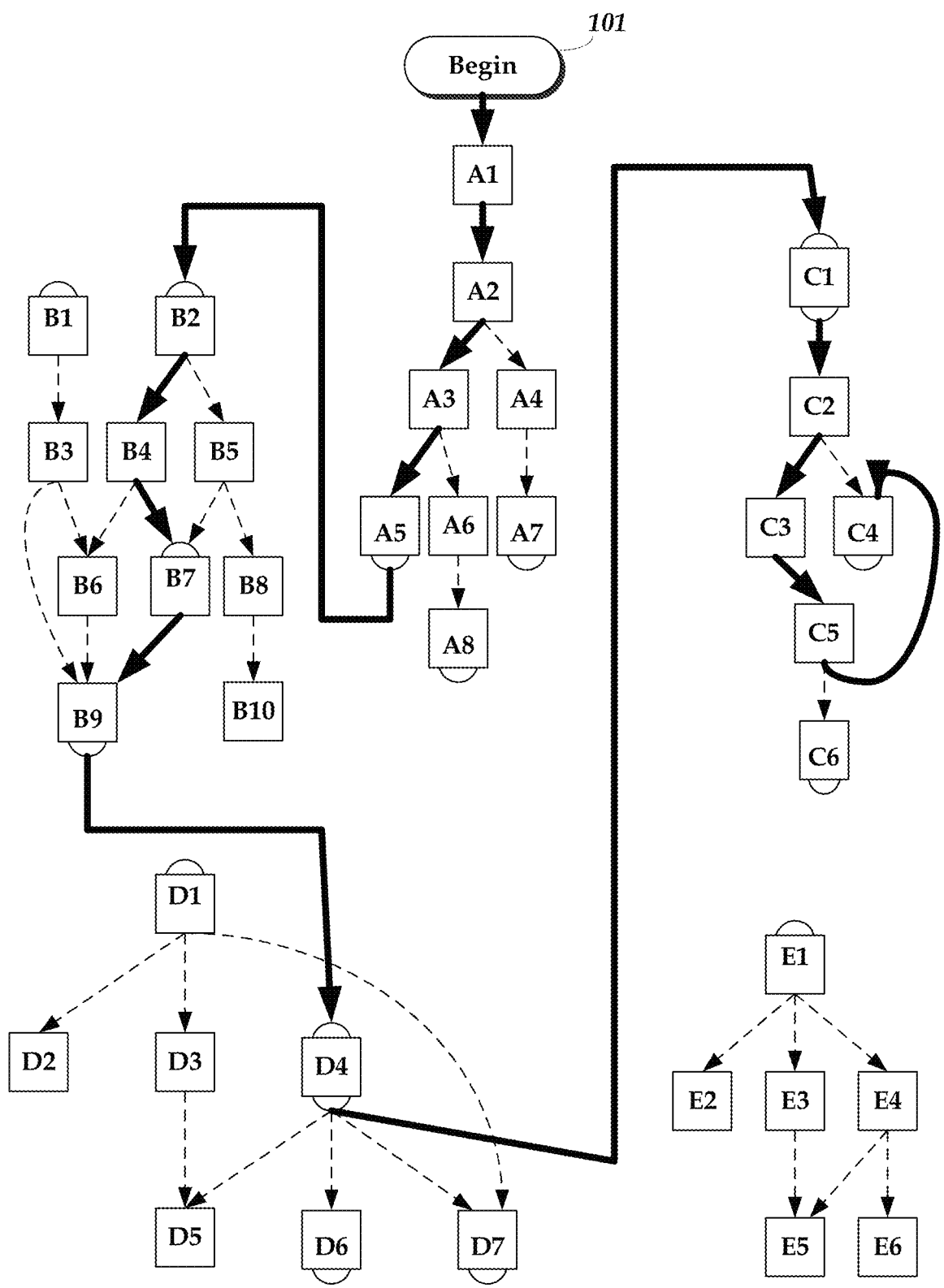
Figure 1D:
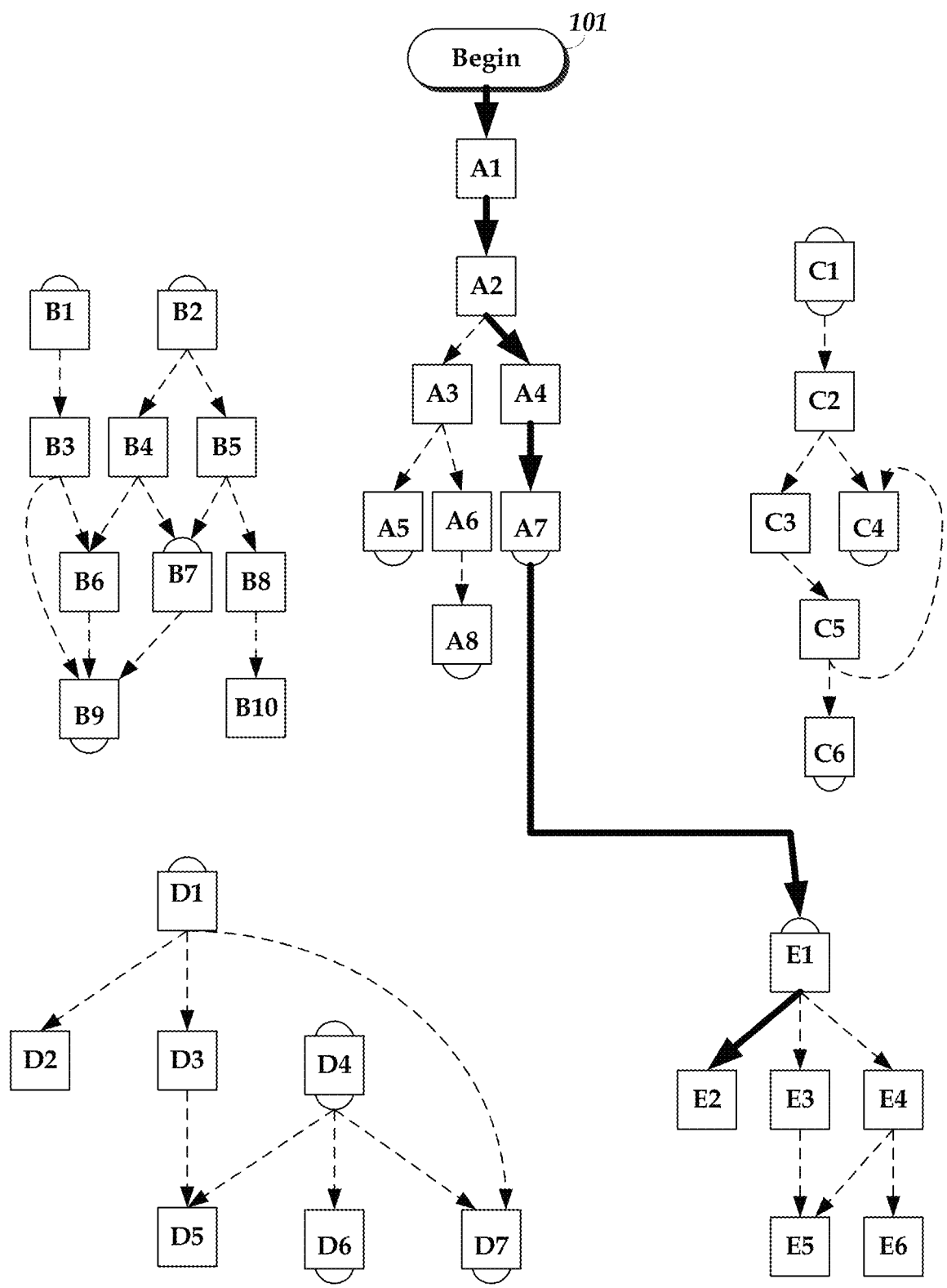

Although the example system may store relationships between some queries, the system may also provide data corresponding to a data acquisition path in which a query is selected despite having no predefined relationship with the prior query. Referring to FIG. 1a, an illustration of a dynamic decision forest is presented. Referring to FIG. 1b, the forest of FIG. 1a is shown in a use case in which clinical inquiries were performed in a data acquisition path. For example, the system may have received responses resulting from user inputs and have determined subsequent responses based at least in part on those received responses, despite the system having no predefined relationship between two responses which occur in series. Data inquiries A8 and C1 in FIG. 1b illustrate an example of such a "jump" between nodes without a predefined relationship. In the present embodiment, the system determines how to "jump" from one query to the other based on the data already acquired, and/or data which remains necessary or useful. As a result, the physician is presented with a series of interfaces which guide a highly informative data acquisition tailored to the particular patient's history and condition. In addition to providing an improved experience by a physician user, the described embodiment's use of jump paths may also allow for a significant number of paths, may provide for a computationally efficient means of storing data used to guide data potential acquisitions, and may reduce the likelihood of system error resulting from improperly predefined query relationships.

Although some of these benefits may seem hidden from the physician user in some embodiments, the physician benefits from the robust system intelligence behind a simplified user interface. Furthermore, in certain embodiments the system may provide verification data which may enable a user to perform an iterative review of previous inquiries. Such iterative feedback may allow for efficient verification of decision data, which may in turn reduce the likelihood of subsequent queries improperly occurring as a result of an improper previous response.

Dynamic Decision Forest

Referring to FIG. 1a, an illustration of a dynamic decision forest is presented. Queries are represented as nodes, with each node identified by a letter-number pair, such as A1, A2, A3, C5, D7, E3, etc. A beginning point 101 is illustrated where the system may start the data acquisition process. Although query nodes A1, A2, A3, A4, A5, A6, A7 and A8 are all interconnected in a tree-like fashion (the "A-tree") nodes in one lettered tree (e.g., the A-tree and the corresponding B-tree, C-tree, D-tree and E-tree) lack a predefined connection with a node in any other tree (for example, the B-tree or C-tree). In the present example, a predefined relationship between nodes is represented by a dotted line terminating in an arrow. Such a relationship represents that a decision path may proceed from one to a node to which it is connected.

For example, referring to FIG. 1a, a decision path would begin at node A1, proceed to node A2, and then proceed to either node A3 or node A4. Each node represents a query, such as a clinical query. In the present embodiment, a clinical query consists of at least a clinical inquiry and a plurality of response options. Some clinical queries may be designed to elicit a single response from a list of response options (for example, by presenting the response options as a radio-button interface where only one response may be selected at any time) while other queries may be designed to elicit one or more responses from a list of response options (for example, by presenting the response options as a check-box interface where multiple responses may be selected at any time). Other types of nodes, inquiries, and/or responses may additionally or alternatively be used.

In the present embodiment, in order to complete a node and proceed to a next node, the system would transmit data concerning the current node's clinical inquiry and receive data representative of the user's selection of one or more response options. In another embodiment, the user's response options may include text, audio, picture, video or other data. For example, a picture response may be provided to document a patient's state at the time of the medical interview. Once the data for the present node has been received, the clinical data acquisition may proceed to the next node. Often, a subsequent node will be selected based at least upon data received from previous inquiries, and pre-defined clinical paths. For example, if node A2 relates to an inquiry in which the patient is asked whether their symptoms are (1) better than the previous visit or (2) equal to or worse than the previous visit, then the system may proceed to node A3 if it receives data indicating a response that the symptoms are better than the previous visit, and may proceed to node A4 if it receives data indicating a response that the symptoms are equal to or worse than the previous visit. In other examples, the system may proceed along a pathway if a numeric response to clinical inquiry is within a certain numeric range, and proceed along a different pathway otherwise. In the embodiment shown in FIG. 1a, the system will occasionally proceed from one node to another node for which there is no predefined path relationship, as will be explained further.

FIG. 1a illustrates an embodiment in which certain nodes are classified as "jump source" nodes and "jump destination" nodes. For example, nodes with a top semi-circle (B1, B2, B7, C1, D1, D4 and E1) are jump-source nodes. For example, nodes with a bottom semi-circle (A5, A7, A8, B9, C1, C4, C6, D4, D6 and D7) are jump-destination nodes. In embodiments such as the FIG. 1a illustration, the system may perform a jump from any jump source node to any jump destination node. In other embodiments, any node may function as either a jump source or jump destination node. In some embodiments, certain nodes may function as both jump source nodes and jump destination nodes. For example, node C1 is both a jump source node and jump destination node. The E-tree lacks any jump source nodes, so according to the illustrative embodiment in FIG. 1a, a decision path which leads to the E-tree would terminate in the E-tree as there could be no jump to another tree. It will be understood that the use of the term "node" does not imply any specific data structure and does not in any other way limit the invention. For example, in some embodiments a relational database may be used and nodes may correspond to entries in that database. In another embodiment, a linked list of data structures may be used. In still another embodiment, an array of flag bits may be used and a node may be represented by a single element of the array. The term node serves to express a basic concept which may appear in a dynamic decision forest present in certain embodiments.

System Architecture

Figure 2:
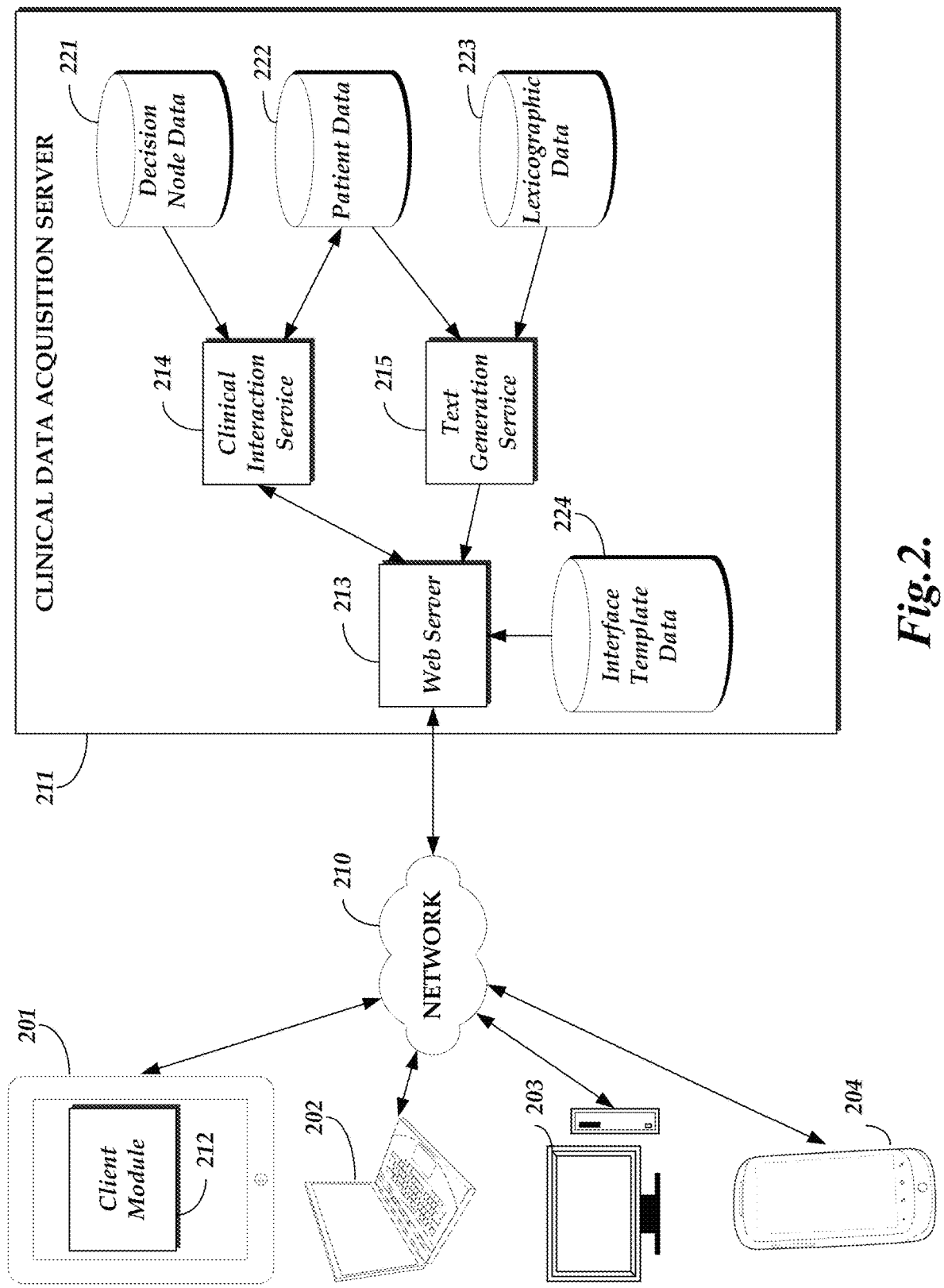
FIG. 2 depicts one embodiment of a system capable of gathering clinical information using a dynamic decision forest and generating natural language descriptions of gathered clinical information.

A dynamic decision forest may be implemented in a number of different embodiments, which could make use of different hardware (e.g., local servers, web servers, desktop computers, laptops, tablet devices, smart phones, etc.) and/or different software, such as different programming languages, interface styles and/or network protocols. FIG. 2 depicts one embodiment of a system capable of gathering clinical information using a dynamic decision forest and generating natural language descriptions of gathered clinical information. In the illustrated embodiment, one or more client devices 201-204 access a clinical data acquisition server 211 through a network 210. Exemplary client devices include a touch-sensitive tablet computing device 201, a laptop 202, a desktop computer 203, or a smartphone 204. Other client devices may also be used. A client module 212 may be provided for use on a mobile client. In some embodiments, a client module 212 may comprise an application stored and executed locally on the mobile client. In other embodiments, the mobile client accesses the clinical data acquisition server without needing to install any new software, for example by using a web-based interface. Alternatively or additionally, a client module 212 may comprise software such as a script-based programming language, provided by the clinical data acquisition server. In another embodiment, the client module 212 may be a web browser accessing network-based menu pages in HTML, XHTML, and/or XML.

In the embodiment of FIG. 2, a clinical data acquisition server 211 comprises a number of components. These include a web server 212, a clinical interaction service 214, a text generation service 215, a decision node data store 221, a patient data store 222, a lexicographic data store 223, and an interface template data store 224. The web server 213 may provide data to mobile client devices 201 in response to network requests. For example, the web server may transmit data to a mobile client device using the Hypertext Transfer Protocol (HTTP). In other embodiments, a different type of server may be used—for example, one configured to respond using a protocol and/or port designed for the system.

The web server 213 receives interface template data 224 from a data store. That template data may include, for example, webpage templates such as HTML and/or CSS files which may be used in combination with specific menu data, so that the menu data can be transmitted to the user in a selected format. For example, font size, font color, text distribution within a page, and other visual elements may be affected by interface template data.

The web server may 213 also interact with a clinical interaction service 214. In this embodiment, the clinical interaction service receives a user input event via the web server, processes the event in order to determine its relationship to the ongoing diagnosis, and then determines the next step in performing the diagnosis. For example, the clinical interaction service 214 may determine that, based upon already stored data, and the most recent user input, a jump should be performed to another node. Such a decision could result in the clinical interaction service transmitting data to the web server indicative of the node selected as a result of the jump process, as described above. At other times, the clinical interaction service 214 may determine that a non-jump node selection should occur, or that a diagnosis has been reached and no further requests for user input should occur.

The clinical interaction service 214 may be in communication with decision node data 221 which may be kept in a data store. It will be understood that any one or more of a variety of possible data stores may be used for all data stores illustrated in this embodiment, and for data stores used in other embodiments. Examples of data stores include a SQL database, relational databases, other types of databases, tables, and/or flat files. Also, while FIG. 2 illustrates multiple data elements 221-224, in some embodiments these may be stored within a single data store, while in other embodiments one or more may be stored in separate data stores. The decision node data 221 may store data representative of a decision node forest, such as that shown in FIG. 1. The clinical interaction service 214 may receive data from the decision node data 221 which the clinical interaction service 214 may then use in determining the next clinical interaction step, such as the next node for the path being followed in the present clinical examination.

The clinical data acquisition server 211 may store patient data 222. Such patient data 222 could include data acquired by interaction with other systems (for example, importing a medical history from another system), data stored from the user physician's previous interactions with the patient, and the already-completed steps of an ongoing medical diagnosis. The system may store response to queries, such as menu entries, as data within the patient data 222. The clinical interaction service 214 may therefore transmit data to the patient data store 222 for storage, and may receive data from the patient data store 222. As the clinical interaction service receives a new user input, it may reference the decision node data 221 in order to determine what possible next steps are available, and then reference the patient data 222 in order to determine which next step is appropriate in for the particular case at issue.

The clinical data acquisition server may also include a text generation service 215. The text generation service 215 may provide descriptive text, such as in sentence or paragraph form, and may be adapted for a specific language such as English. The text generation service 215 may be capable of receiving patient data 222 and lexicographic data 223 in order to determine the lexicographic and grammatical structure of data which the service 215 may then output to a web server 213 to be transmitted to a user device 201. Lexicographic data may indicate rule sets for a particular human language, including information about grammatical relationships between different word types. Such data may be stored in any of a variety of formats, and may be designed to facilitate translating patient data into human understandable text.

Although FIG. 2 shows certain components of a decision forest system, it will be understood that a number of other embodiments may also or alternatively be used. For example, the entire system may be run locally on a single device. In such an embodiment, there may be no need for a network and a division of client module from clinical data acquisition server. In another embodiment, data stores are located on separate hardware than the services which interact with them.

Menu Sequencing

In some embodiments, a system using a dynamic decision forest presents user input prompts, such as through an interactive menu system. The system may then receive a user response based on the user's selection of one or more menu items. Alternatively or additionally, the system may obtain user input through other interfaces or methods. Some such embodiments may include lexicographic logic functions whereby information presented to a user, prompts presented to a user, and/or information received in response to user input may be based in part on lexicographic rules.

For example, a system may include logic for parsing lexicographic items, identifying grammar, and/or classifying words. Considering the example of a physician user of a medical dynamic decision tree system, the system may behave based on lexicographic structure of the physician and/or patient's language, such as English. One of the interesting features of the English language is that the order in which descriptive words and phrases appear in a sentence is not necessarily the same as the order in which the physician might acquire those data items during a consultation. An embodiment of a dynamic decision tree system with menu interaction may therefore present menus in an order and context that a physician will be expecting even though this may not be most convenient for generating text.

Figure 3:
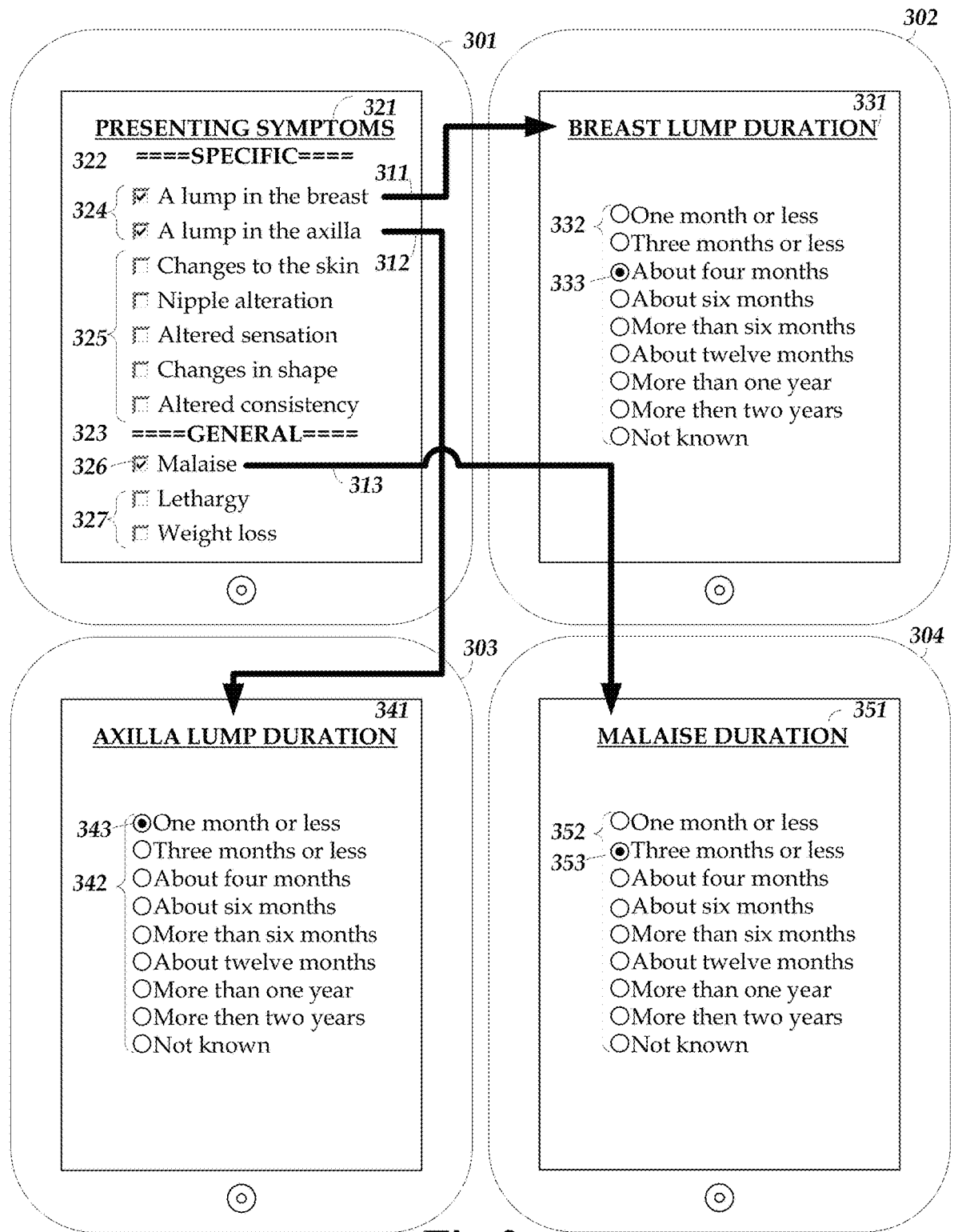
FIGS. 3 and 4 illustrate example user interfaces for receiving clinical information. The figures' arrows illustrate the effect of data entry on the presentation of future user interfaces.

For example, referring to FIG. 3, an embodiment is shown in which the system provides a user with menu-driven prompts for input. Four menus are shown 301-304. Each menu consists of a prompt 321, 331, 341, 351 and menu response options. In the first menu 301 the menu prompt requests that the physician user identify the presenting symptoms of the patient 321. The menu response options are categorized as either specific symptoms 321 or general symptoms 323. The specific symptom options shown are "a lump in the breast," "a lump in the axilla," "changes to the skin," "nipple alteration," "altered sensation," "changes in shape" and "altered consistency." The general symptom options shown are "malaise," "lethargy" and "weight loss." In FIG. 3, for the first menu 301 within the sequence, two specific symptom options 324 and one general symptom option 326 have been selected. For example, this embodiment may present the physician user with the ability to select symptom options and/or other menu-based response options through a touch screen interface of a tablet computing device. In other embodiments, other computer systems are used. The system in the present embodiment determines which menu prompts to display to the user based upon the received input and/or other stored data.

For example, in FIG. 3, the system presents a second menu 302 titled "Breast lump duration" 331, based on receiving user input in the first menu 301 which indicated the presence of a lump in the breast 324. The arrow between the first and second menu 311 indicate this causal relationship. Relating this to FIG. 1b and the system's behavior of traveling between nodes, the arrow 311 corresponds to a transition from one node to a second (e.g., transition 112), whether those node had a predefined relationship (e.g., transition 112), or the transition was a jump (e.g., jump 114). The second menu 302 includes a number of response options 332, but allow for only a single response to be selected at any time. In FIG. 3, the selected response is "About four months" 333. In the illustrated example, radio buttons 332, 342, 352 indicate when only one response may be selected for a given menu and checkboxes 324-327 indicate when multiple response options may be selected for a given menu. In other embodiments, other methods of indicating input options and/or recording input events may be used.

FIG. 3 contains third 303 and fourth 304 menus, titled "axilla lump duration" 341 and "malaise duration" 351, respectively. The system may present these menus based on the responses given in the example first menu 301. For example, the selection of "a lump in the axilla" 324 results in the system seeking additional data concerning the lump, shown by the transition arrow 312. In the present embodiment, three items 324, 326 have been selected in the first menu 301 which cause additional menu screens 302-304. In one embodiment, the subsequent menus are shown in the order that the triggering user inputs appear in the earlier menu 301. In another embodiment, the subsequent menus are shown in the order that the user input events occurred which selected those items in the first menu 301.

Figure 4:
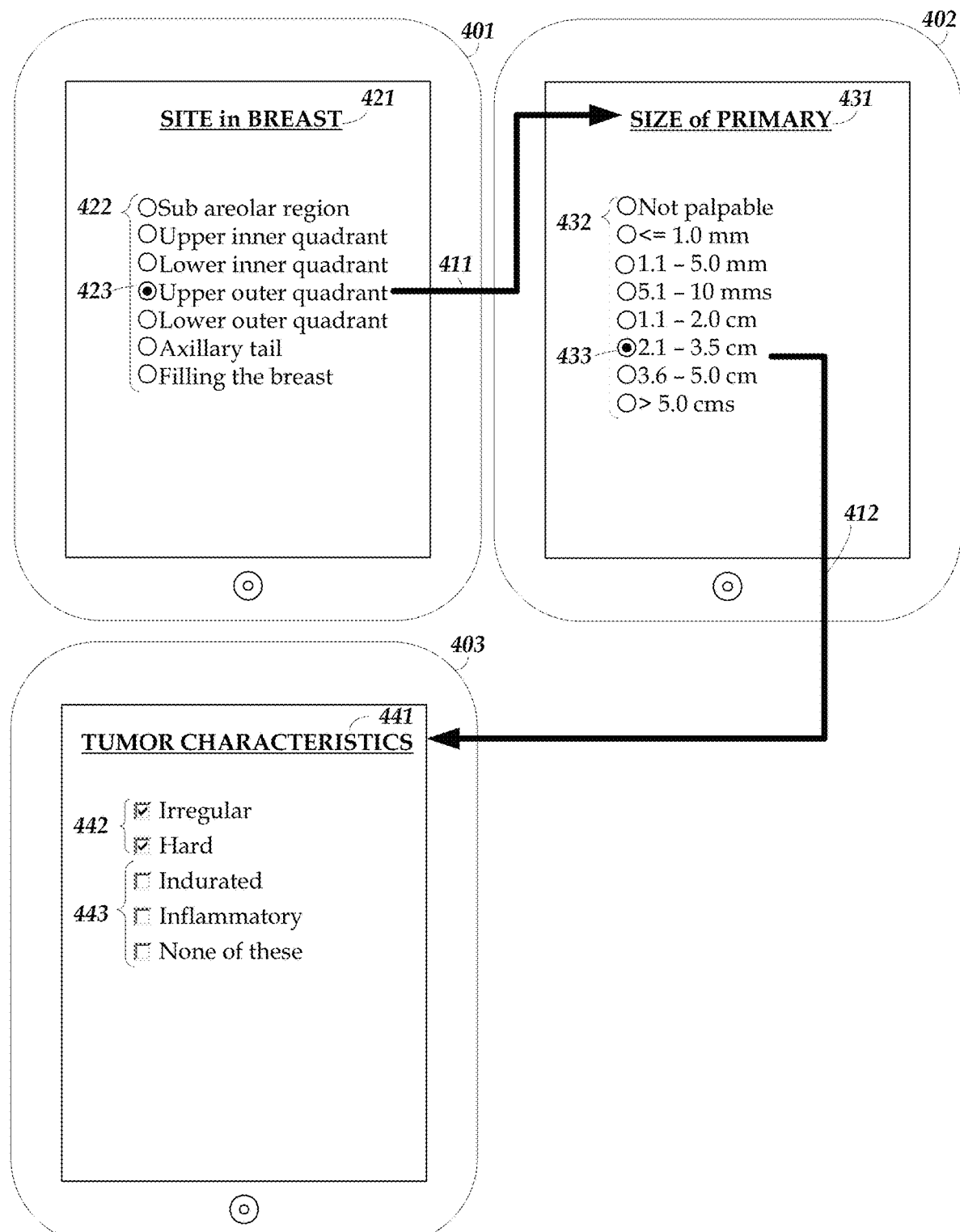

Referring to FIG. 4, additional examples of menu interfaces are provided 401-403. Here, three menus occur in sequence, as an input from the first menu 423 causes a transition 411 to the second menu 402. There, an input 433 causes a transition to the third menu 412.

Figure 5:
FIG. 5 illustrates an example user interface for receiving verification information concerning previously received clinical information.

Referring to FIG. 5, an input verification screen is presented 501. The system may present a summary of information recently received and stored, thereby allowing a user to review for any mistakes. The user may be presented with the ability to edit the input 502, or to verify that the input is accurate and continue 503. In some embodiments, verification occurs as an iterative process whereby at certain pre-designated points during a diagnosis process, the system seeks verification of all input received since the last verification if any. This may allow for verification at short intervals which may increase the likelihood that the user will remember their input and be able to recognize if an improper value has been entered. In another embodiment, verification points are not pre-designated, but are dynamically determined at run time—for example, occurring after every 7 menu interfaces.

Referring to FIG. 6, an example of text generated by the system is presented. The received input is described as a history of present complaint 601, with a multi-sentence description 605 incorporating both received data and lexicographic rules for the English language. The interface shown in FIG. 6 further allows the user to enter free text 603 (described further below), to edit 602 menu inputs used in the text description, or to verify the note and continue 604.

In a use case for another embodiment, the system has presented a user with seventeen (17) menus and received twenty-four (24) menu responses. The system then generates the following text based on the received input data. The example illustrates lexicographic capabilities which some embodiments of a dynamic decision tree system may include for generating text output. The input data indicated, in the order which their corresponding menus appeared:

(1) PRESENTING SYMPTOMS: a lump in the breast, a lump in the axilla
(2) BREAST LUMP DURATION: about four months
(3) AXILLARY LUMP DURATION: one month or less
(4) SITE IN BREAST: upper outer quadrant
(5) SIZE OF PRIMARY: 2.1-3.5 cm
(6) TUMOR CHARACTERISTICS: hard, irregular
(7) LUMP CHARACTERISTICS: painless
(8) SURROUNDING BREAST: tender
(9) LUMP CHARACTERISTICS: fully mobile
(10) BREAST CUP SIZE: medium-large—D cup
(11) LOCAL SPREAD: none
(12) IPSILATERAL AXILLARY NODE STATUS: one node
(13) MARKER NODE SIZE ESTIMATE: 1.5 cms
(14) NODE MOBILITY: fully mobile
(15) ADDITIONAL NODES: none
(16) CONTRALATERAL BREAST: normal
(17) ANY CLINICAL SUSPICION FOR DISTANT METASES: no.

The format of the above menu sequence is such that each line corresponds to a different menu input presented by the system, numbered in sequential order. The title of the menu is presented in capitalized letters, and the user-selected input is provided after the colon, with multiple-input selections separated by commas. This use scenario will be further described in order to provide an example of text generation from menu driven input.

In the present example, the system may then generate the following text based upon the above-described menu entries: "On examination a lump was found in the upper outer quadrant of the right breast that measured between 2.1-3.5 cm and on palpation this was hard and irregular but, not indurated or inflammatory. The lump itself was painless but the surrounding breast was tender. The mass was fully mobile within a medium-large, D cup breast with no spread to local structures. On ipsi-lateral axillary examination there was one lymph node that was fully mobile which measured about 1.5 cms in diameter. There were no nodes palpable in any of the other gland bearing areas and examination of the contra-lateral breast revealed no abnormalities."

As the diagnosis, organ containing the lesion (lump) and the side have been established upstream this series of menus can only pertain to examination of the patient. Hence, the first sentence must start with "On examination . . . ", "When the patient was examined . . . " or some such similar sequence of words where, for convenience, the words other than the menu items are shown in between quotes (" "). The next component of the sentence must be what was found i.e. a lump (established earlier), followed by "was found". The next sequence of primary data units (PDUs) the physician will wish to record will be (a) the site of the lesion in the breast, (b) its size and (c) what does it fell like. These PDUs, are then added to the sentence with addition of "in the" upper outer quadrant "of the right breast" (established upstream), "that measured between" 2.1-3.5 cms "and on palpation this was" hard and irregular. This last menu is multiple-choice and the items that were selected are appended to the sentence in a loading algorithm. An additional algorithm used here also appends the items that were not selected. Hence, the phrases "but, not" indurated or inflammatory are also appended.

If the selection in menu (6) described above had been "hard, irregular and indurated" the output from the two loading algorithms appending to the sentence would have been "hard, irregular and indurated but not inflammatory".

Having completed the 1st sentence in this example scenario, the system's text generation may next generate text for the 2nd and 3rd sentences which, for convenience are reproduced here. "The lump itself was painless but the surrounding breast was tender. The mass was fully mobile within a medium-large, D cup breast with no spread to local structures." The text-generating menus for this sentence correspond to the menu sequence (7) through (12) described above. As a manner of providing background to one use of the system, cancerous lumps, particularly in the relatively early stages, are almost always painless because they do not contain nerves. They only become painful with pressure and/or destruction of the nerves within the organ of origin. Embodiments of the system may include menu based sequences based on such subject-specific information. Logically, menu (3) should follow (1) because the PDUs in both of these menus pertain to characteristics of the lump. But, the physician may wish to compare and contrast any pain associated with the lump and the breast hence, menu (2) follows (1). The system in the present embodiment may then generate the 2nd sentence as: "The lump itself was" painless "but the surrounding breast was" tender. The system may also construct sentence 3 with the 3 key terms fully mobile, medium-large, D-cup and no with the responses from menus (3), (4) and (5), respectively. The first of these pertains to the lump, the second to the breast and the 3rd to local structures.

Hence, the sentence can be constructed as: "The mass was" fully mobile "within a" medium-large, D cup "breast with" no "spread to local structures."

The mobility and size of the mass (synonymous in this context with lump, lesion and a number of other descriptive terms) in relation to the size of the breast is important for determining what surgery, if any, can be carried out.

The last two sentences contain seven key words from only five single choice menus which are shown above as menus (13) through (17). On ipsi-lateral axillary examination there was one lymph node that was fully mobile which measured about 1.5 cms in diameter. There were no nodes palpable in any of the other gland bearing areas and examination of the contra-lateral breast revealed no abnormalities.

The response from (12) was one lymph node and the header contains the key terms ipsilateral and axillary hence the beginning of sentence can be constructed with "On ipsilateral axillary examination" there was "one lymph node". The responses from menus (13) and (14) were 1.5 cms and fully mobile respectively which is the order in which physicians historically gather those points of information. But, the order in which these data will often be dictated or written is the reverse. Hence, the remainder of the second sentence will be "that was" fully mobile "which measured about" 1.5 cms "in diameter." The last sentence is generated from the responses no and normal from menus (16) and (17) respectively. The system then completes the paragraph as: "There were" no "nodes palpable in any of the other gland bearing areas and examination of the" contra-lateral "breast revealed" no abnormalities (the menu item normal is synonymous with no abnormalities)

Although the above-described use scenario for menus (1) through (17) includes specific sequences, menus, input options, and lexicographic rules it will be understood that many other sequences, menus, input options and lexicographic rules are within the scope of various embodiments of a dynamic decision forest.

Iterative Verification

The embodiment contains a two page verification system which is engaged on completion of each data capture segment that enables the user to check the input for errors. The first of these pages has 4 buttons namely "all OK and continue", "all OK and STOP", "add free text" and "re-start this section." Upon receipt of an "all OK and continue" message, the system may continue with transmitting new menu data, for example the system may store the generated text on disk then continues to the next section. Upon receipt of an "all OK and STOP" message, the system may stop transmitting menu data, for example the system may stop after writing the currently considered text to disk. Upon receipt of an "add free text" message, the system may present the user with the ability to enter in text, such as through a free-form text field. In some embodiments, this may be characterized as a "Free Text input" or "FTI." In one example, the system accepts FTI in 16 lines each of 80 characters—corresponding to about half a page of type written text. In other embodiments, other text restrictions or no text restrictions may be used. That text may be stored by the system and integrated into note text generated by the lexicographic service. Upon receipt of a "re-start this section" message, the system may re-transmit menu data for the most recent menu section.

In the present embodiment, on FTI completion the system displays the user's contribution and requests confirmation with two buttons namely, all OK and re-enter free text input. If the 1st is pressed the program appends the user input text to the computer generated text and, again, stores this on disk before proceeding to the next section. However, there is one caveat when entering free text that pertains to control characters that have special significance for the program's data management systems with browsers using HTML, XHTML and XML, which is effectively all of them. These characters are the ampersand (&), the hash character (#), the pipe character (I) and tilder (~). The ampersand and the hash character are used in combination in the system as &#nnn (nnn is a 3 character numeral) to encode characters that do not appear on regular keyboards. In this embodiment, these invisible characters are used as data separators and the &# combination should not be used in the free text input fields. This restriction should not constitute a problem and both of these characters should be able to be used separately but, just to be on the safe side try to avoid using the ampersand and use and instead. In other embodiments, other text formatting is used which does not include such special character restrictions. In still other embodiments, text editing software such as Microsoft Word or Open Office Writer may be integrated with the system for text entry.

Pressing the re-enter free text input at the 2nd verification wipes the free text input and enables you to re-enter corrected text. Pressing the re-start this section button at the first verification step re-sets the data stream to that recorded at the beginning of that particular section which enables a re-start of the whole section to be made.

Interface Based on Human Cognitive Numeric Limitations

As mentioned above, in some embodiments, iterative feedback occurs in a dynamic, calculated manner. For example, the theory of Miller's number states that most persons can keep between 5 and 9 objects in their working memory at any given time. In one embodiment, the system requests verification after each sequence of approximately 7 menu screens. In other embodiments, other iterative rates are used, or approximate rates are used. In other embodiments, verification points may be pre-defined. In still other embodiments, other algorithms may be used to dynamically calculate verification points—for example by weighing a variety of factors such as number of entries per menu page, time elapsed, number of menus since previous verifications, and/or other factors.

Raw Data Collection and Audit Trail

One embodiment of the system uses raw data collection that can be used in an audit trail or in data re-construction. These data are collected in a file separate from the various text data files and contains the page name, its sequence number and the numerical response from the text-generating menu pages. If the page is non-text-generating (i.e. NO menu), the item collected is 'nul' instead of a numerical value. Each record is separated by the 'pipe' (|) symbol. This file is stored on a server together with the text files and in duplicate in a separate domain as a system backup. The text files can be re-generated from this raw data file backup should a 'disaster' befall the servers. This is a very unlikely eventuality as the whole system is HIPPA compliant and the data are stored on two servers in separate locations.

In addition, the 'raw data' file contains two key items. The first is a 256 bit 'long-word', called vBits, that employs single-bit logic to record which clinical items have been completed. The second is a listing of the clinical items in the system, clinList, and the order in which the physician wishes these to be printed out. The latter is used in the pathway logic to determine which items are located in which particular path in the system. Whereas, the bits set from zero to unity in vBits have fixed locations for each clinical entity, the order of the clinical entities in clinList is variable and user-determined for each patient.

Think Ahead Functionality

Figure 7A:
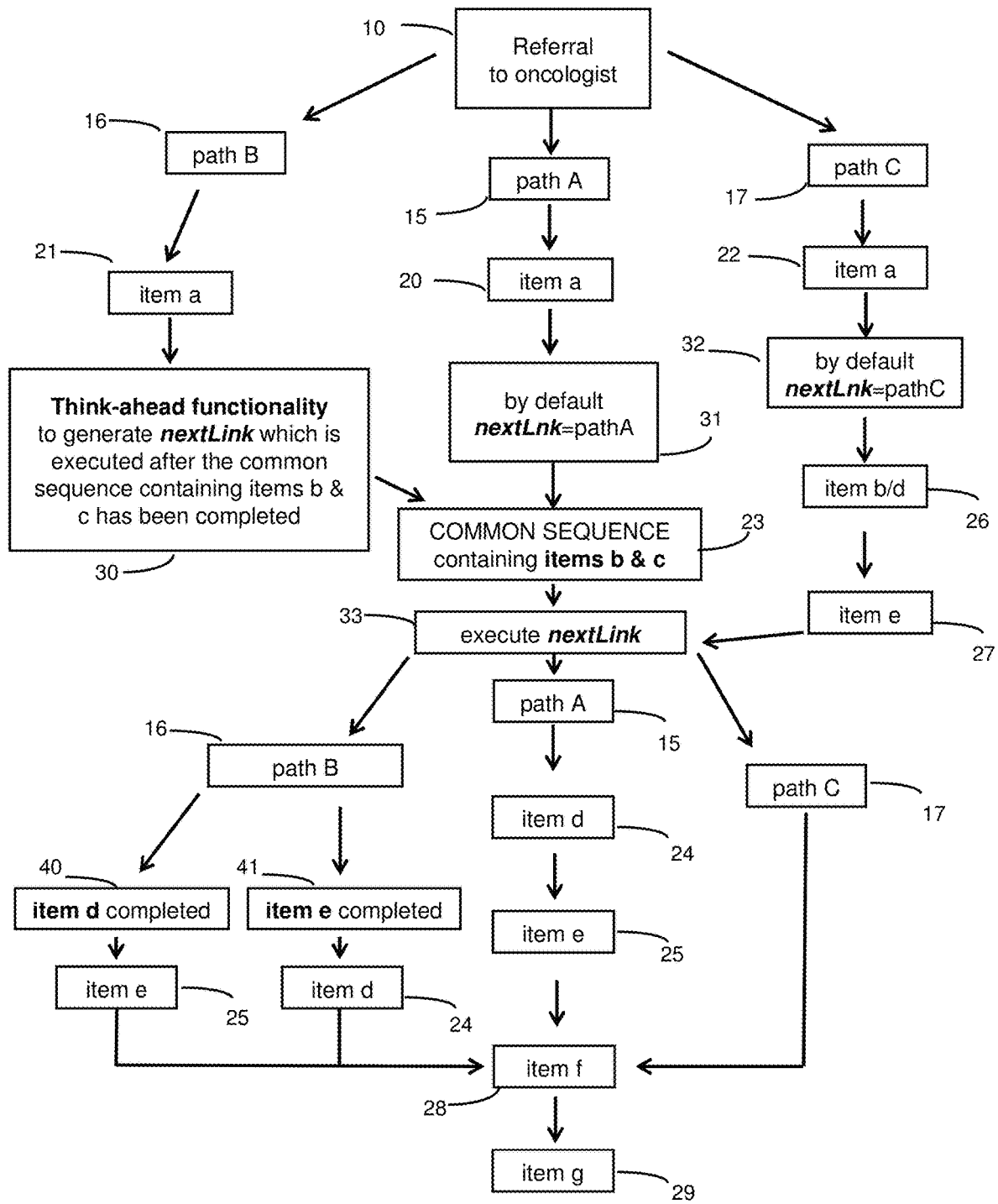
FIGS. 7a-7e depict information acquisition steps which may be performed by a dynamic decision forest, including different paths which may be followed during various uses of that dynamic decision forest.

In some embodiments and use cases, jump paths may be triggered in certain situations, for example if the patient is to be scheduled for radical (curative) treatment. In some embodiments, the fact that a jump will be taken within a dynamic decision forest can be determined a number of steps before the jump actually occurs. This may be referred to as "think ahead" functionality. For example, referring to FIG. 7a, there is a total of 6 elements in paths A and B but only 4 in path C that need to be completed and these are represented by items a through f, 21 through 29 respectively (in reality there are over 100 such items). The last element, item g 29, is the end-point that represents the treatment prescription. The first item, a (20, 21 & 22), represents the history of present illness/complaint and is common to all three paths but, the structure is different in each hence these are labeled 20, 21 & 22 as only the 'name' is common. The sequence depicted in path C 17 is entered if the patient requires treatment for metastatic disease where b and c are not needed.

Figure 7B:
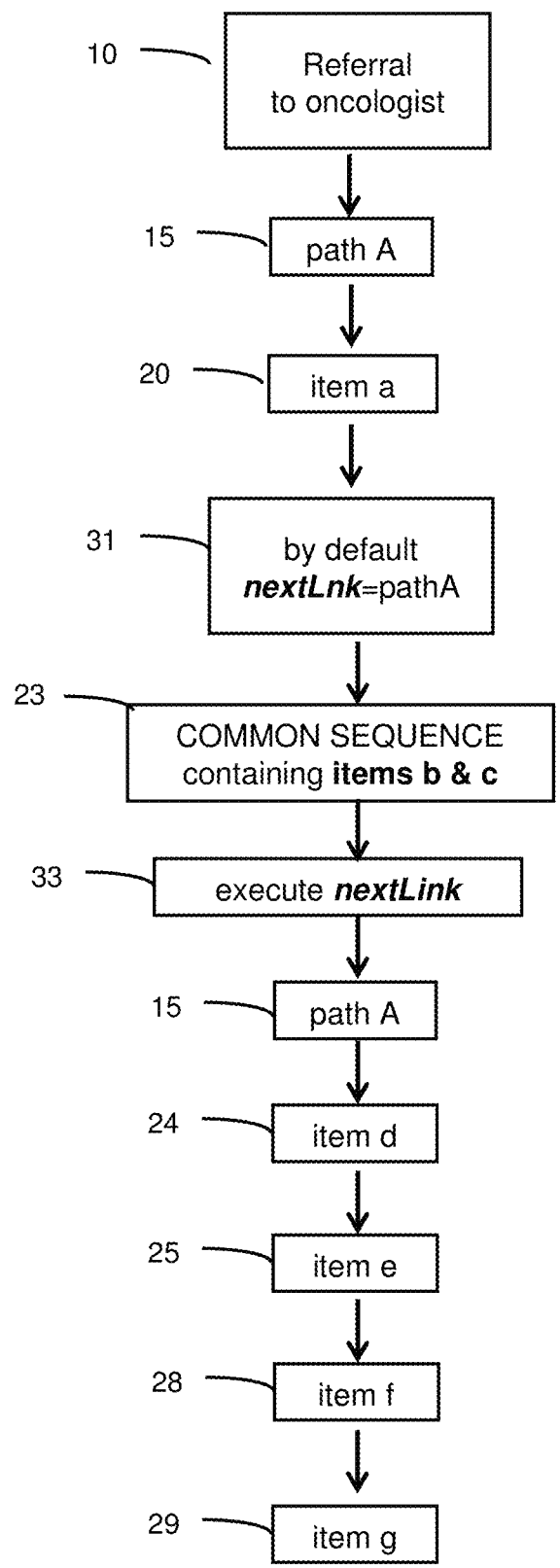

FIG. 7b represents the events that would be engaged by the system if the patient was scheduled for radical treatment after referral to an oncologist by a family practitioner, or a self-referring patient, where no definitive diagnostic procedures (e.g. diagnostic imaging or biopsy to establish the disease stage and diagnosis) had been carried out.

Because item d 24 and item e 25 have not been carried out the system enters path A 15. After recording item a 20 the system sets nextLink to the default, which is the current path, A 15 at 31. It now enters the common sequence 23 where items b+c 23 are completed and then continues down path A 15 after execution of nextLink at 33.

Figure 7C:
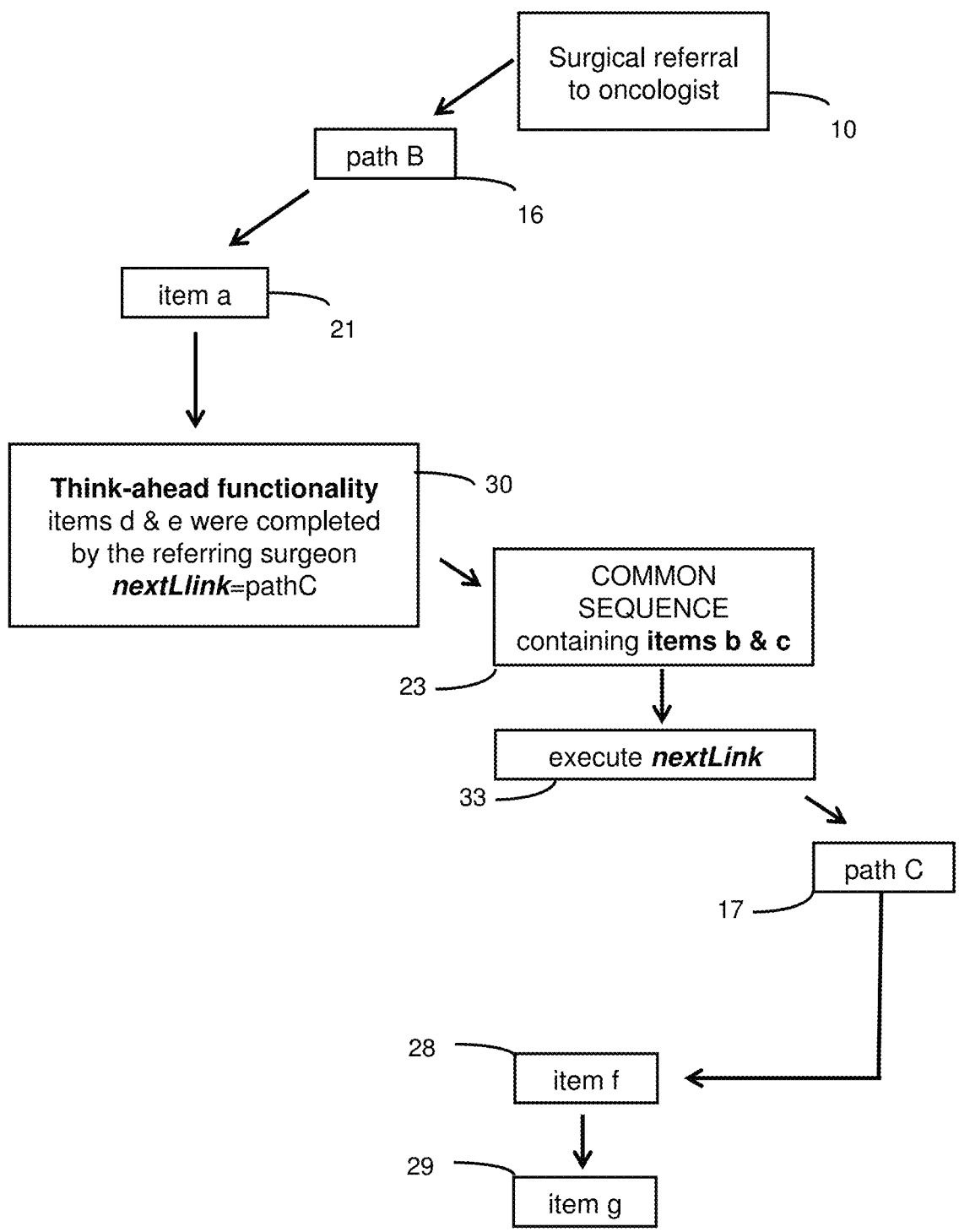

FIG. 7c The system enters the radical treatment path B16 if the referring surgeon has already carried out both the items d and e, 24 & 25 (e.g. diagnostic scan and biopsy to establish the diagnosis and disease stage). The relevant clinical data are recorded from the referral letter after establishing and recording the history of present illness (item a 21) from the patient and the referral letter.

The system now switches the appropriate bits in the 'long-word', vBits (see page 26, 'RAW DATA' COLLECTION and AUDIT TRAIL), corresponding to items a, d and e (21, 24 and 25) from zero to unity which tells the system that these items have been completed. It now 'knows' that items b+c and f (23 and 28) need to be completed before treatment can be prescribed at item g 29.

Items b+c 23 are located in the common sequence 23 and the system also 'knows' not to enter path A 15 after completing the common sequence at 33 because items d and e (24 & 25) have already been recorded as this avoids duplication. Furthermore, it 'knows' that item f 28 is located in the tail-end of path C 17 hence, the think-ahead functionality 30 sets the variable nextLink to path C 17 before entering the common sequence 23. When the latter has been completed the system executes nextLink at 33 to enter path C 17.

Figure 7D:
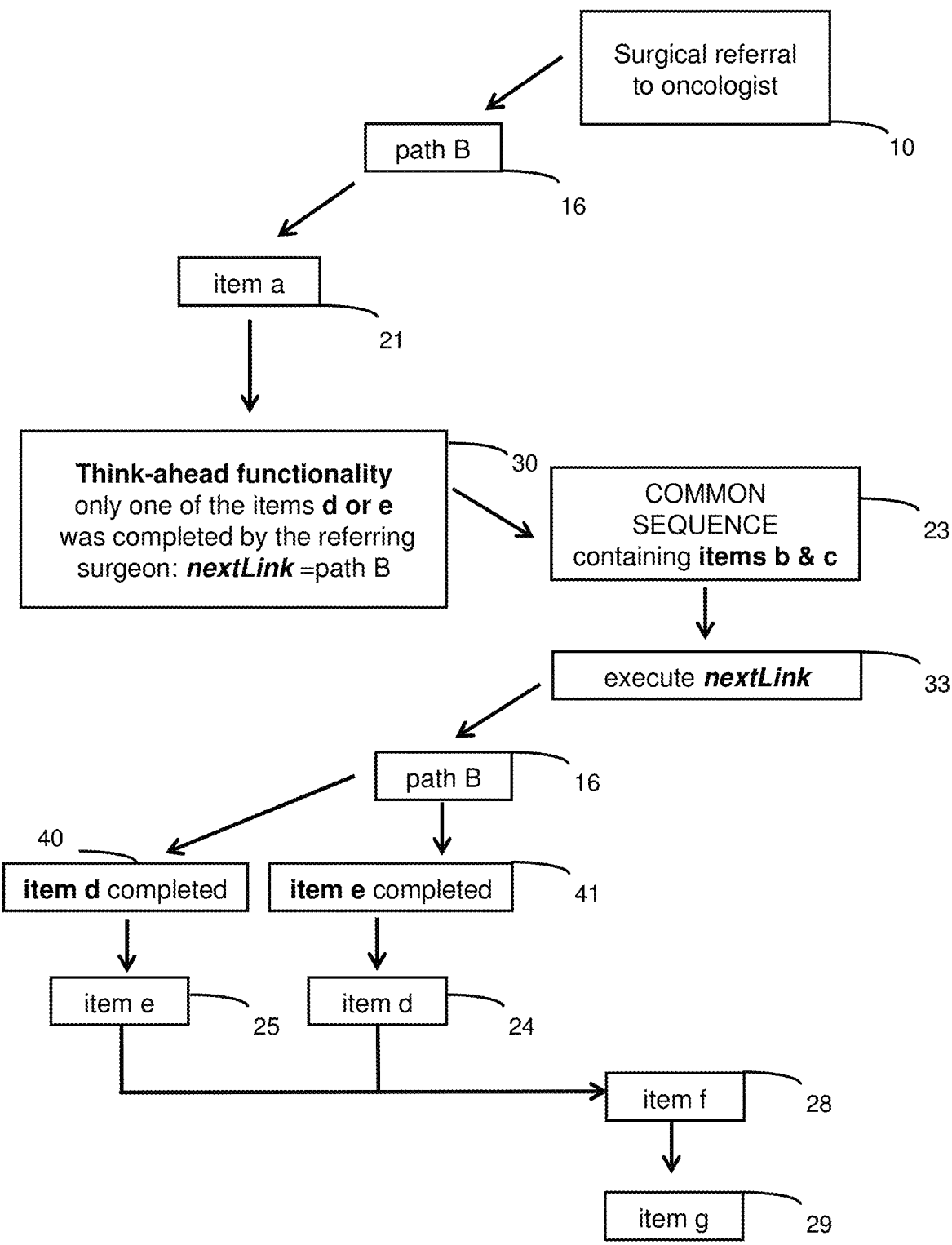

Referring to FIG. 7d, the system also enters the radical treatment path B16 if the referring surgeon has carried out only one, but NOT both, of the items d and e, 24 & 25 (e.g. diagnostic scan and biopsy to establish the diagnosis and disease stage). Again, the relevant clinical data are recorded from the referral letter after establishing and recording the history of present illness (item a 21) from the patient and the referral letter.

The difference from FIG. 7c is that either item d 24 or item e 25 must be completed before reaching item g 29. Again, the appropriate bits in vBits are switched from zero to unity (a+d or a+e) to record the completed items. Path A 15 contains both item d 24 and item e 25 which must be avoided to stop duplication and, path C 17 contains neither hence, the system's think-ahead functionality sets nextLink to path B at 30. After the common sequence 23 is completed nextLink is executed at 33 and the system re-enters path B 16 where either item d 24 or item e 25 needs to be completed. The system 'knows' which item, d or e (24 or 25), to complete by reference to the appropriate bit that has not yet been set to unity in the 'long-word', vBits.

Figure 7E:
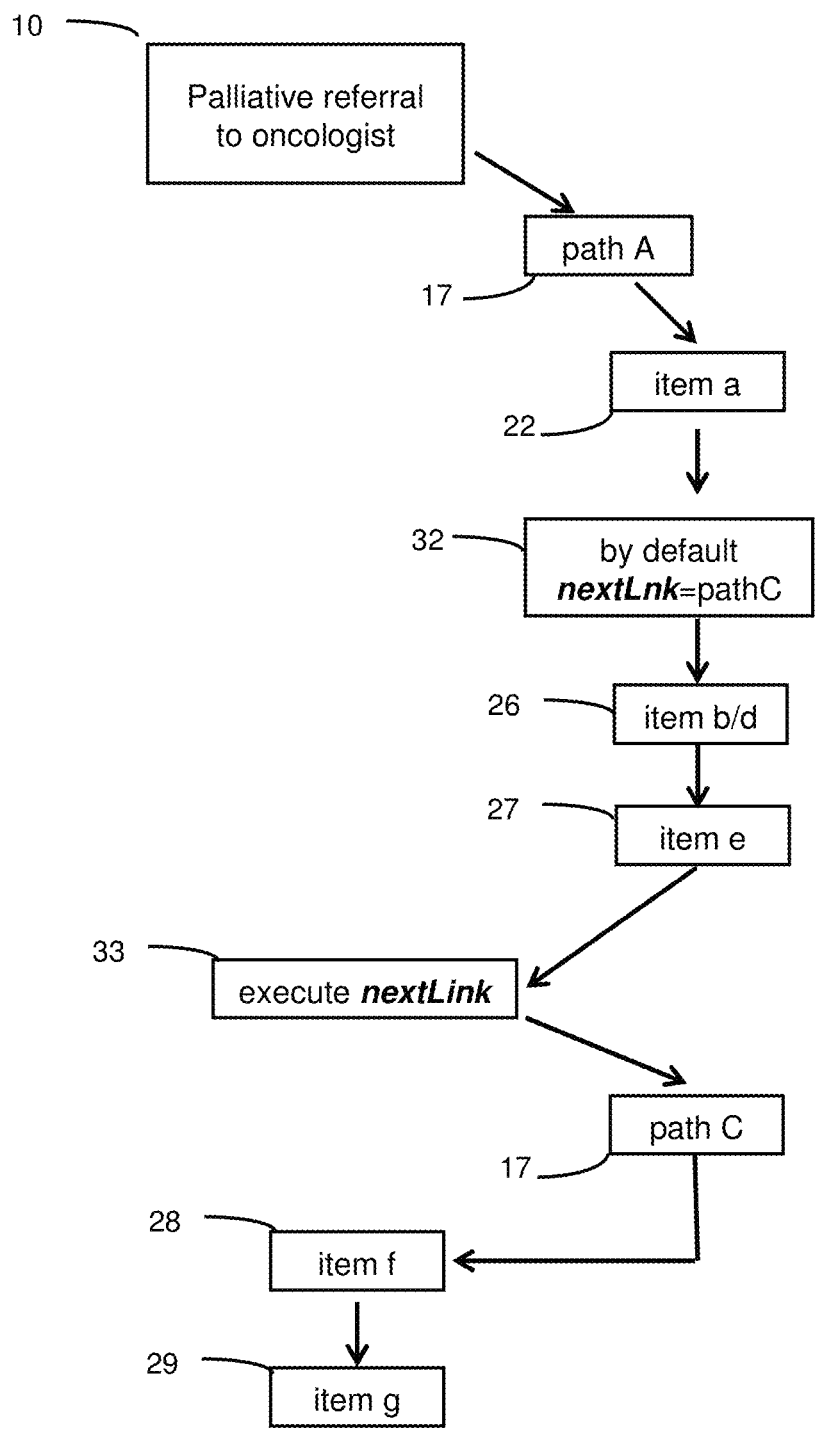

FIG. 7e depicts the referral of a patient with metastatic disease who requires palliative treatment. Only 4 items namely a, d, e and f, 22, 26, 27 and 28 respectively, need to be completed before treatment is prescribed at item g 29. After recording item a 22 the system sets nextLink to the default, which is the current path, C 17 at 32. Items d 26 and e 27 represent brief diagnostic imaging and biopsy reports and these could be by-passed if the patient is known to the physician who already has these data. After execution nextLink at 33 the program re-enters path C 17 and thence to item f 28.

Text Engine

The described embodiment contains a text engine that converts a sequence of "clicked" menu items into fluent text and it has four main requirements. (a) The output must convey meaning, (b) it must be factually accurate, (c) it must be unambiguous and (d) it should not look as if it has been written by a computer.

1) The Menus and Error Trapping

The text-generating menus (the majority) contain descriptive key words or phrases that pertain to specific sections of the medical record capture process. Each menu is presented in a logical sequence and appropriate medical context with which the physician will be familiar. When a menu item (button) is selected (pressed, clicked) the program captures the associated numerical value and stores this (hence, the digital acquisition).

Single choice menus are characterized by radio buttons (round) where only one selection can be made and the multiple choice menus are identified by check boxes (square) where any combination of items can be pressed. In order to reduce the number of mouse-clicks the user has to make, some sets of single choice menus have been placed in a composite menu. This necessarily requires using checkboxes (it is just the way the web works) so it could be possible to click more than one item from a single-choice menu within the composite. However, this eventuality is identified by the system in an ERROR TRAP that tells the user when the combination of buttons pressed is inappropriate and re-sets the menu automatically for data re-entry.

2) The Text Generator

Language is complex and the meaning of the same word can depend heavily on the context in which it finds itself. As an example, consider the 4-digit word live in 4 different sentences.

(a) Does he live in the city ?
(b) Don't touch that wire it could be live.
(c) I know my days are numbered but I really want to live a bit longer.
(d) That girl is a really live wire.

The difficulty here is that the 4-digit string 'live' has no meaning to the computer, it is just a string of characters that is represented by a numerical value in computer memory. Hence, the context within which a word or phrase finds itself is of crucial importance in creating meaning and avoiding ambiguity.

The digital (numerical) data collected by the embodiment represent descriptive words or phrases and it is only possible to generate a fluent text output because of the order in which the content in the various menus is presented to the physician. This is the context within which the buttons are pressed and represents the grammar. The text generator is not contained within a single algorithm but, it is essentially a series of algorithms that construct the text sentence-by-sentence as each sequence of menu items is clicked. On starting the system the program requests the consultant ID (a three letter string), the organ involved (e.g. breast, lung, prostate, colon etc.), the side for paired organs, the consultant's specialty (radOnc, medOnc, sgyOnc, CCC, comprehensive cancer centre etc.), the disease status (i.e. with a primary, local recurrence or metastases) and clinical presentation (de novo with symptoms, post imaging, after chemotherapy, after surgery, for a 2nd opinion/treatment or co-incidental. The system may use some of these data in selecting the appropriate pathway for ongoing data gathering.

Consider the set of menus depicted in FIG. 3-4 that pertain to a breast cancer patient who is presenting with symptoms. Menu 301 contains a list of the most likely presenting symptoms and let us suppose the first two items (primary data units, PDUs) are selected. Menu 302 is engaged next where a breast lump duration of 'about four months' is recorded. Then, menu 1c is engaged to record an axilla lump duration of 'one month or less'.

The sentence can now be constructed from the following elements and although this is the simplest example of text generation by the system it illustrates a number of features.

1) Menu 302 will be entered if (a) the patient has breast cancer and (b) the disease presentation switch 'with symptoms' was pressed which were both established previously. However, the system confirms that it is the correct path by checking against the header in menu 1a which contains the character string presenting symptoms.

2) The descriptive phrases chosen were a lump in the breast, a lump in the axilla, about four months and one month or less that, when taken out of context have no valid meaning as the interpretation could be ambiguous.

3) However, a lump in the breast is associated with menu 302 and a lump in the axilla is associated with menu 303.

4) It is now possible to construct the text with words to the effect "This patient presented with a lump in the breast for about four months and a lump in the axilla that had been present for one month or less."

There are a number of different ways to phrase this sentence and because the lump in the axilla had been noticed for a shorter time than the breast lump it is possible to qualify and emphasize this with the terms "but" and "only" as follows: "This patient presented with a lump in the breast for about four months but the lump in the axilla that had been present for only one month or less."

Audio Bookmarks

In some embodiments, the dynamic decision forest system may store audio data and related audio bookmarks. For example, a mobile device used with the system may include the ability to record audio during a clinical decision process, such as a patient interview. The mobile device may also be used during the clinical decision process to navigate through decision steps, such as through a menu-driven embodiment described above. In such embodiments, an audio bookmark feature may be used which stores data concerning the stage of audio recording which corresponds to certain decision path actions. For example, referring to FIG. 3, such an embodiment may store information flagging or bookmarking the point during the audio recording when the data entry of "About four months" 333 occurred in the second menu 302. In some embodiments, this bookmark may take the form of a timestamp associated with a data entry for the menu selection. In other embodiments, pointers or other forms of storage may be used. The system may then enable a user to select an audio replay of the recorded audio corresponding to a desired portion of menu input. For example, the physician, when reviewing the note, could easily listen to the patient's reaction at around the time the menu input was entered for menu 302.

CONCLUSION

The system, such as the FIG. 2 embodiment, may be implemented as a computing system that is programmed or configured to perform the various functions described herein. The computing system may include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium. The various functions disclosed herein may be embodied in such program instructions, although some or all of the disclosed functions may alternatively be implemented in application-specific circuitry (e.g., ASICs or FPGAs) of the computer system. Where the computing system includes multiple computing devices, these devices may, but need not, be co-located. The results of the disclosed methods and tasks may be persistently stored by transforming physical storage devices, such as solid state memory chips and/or magnetic disks, into a different state. Each service described, such as those shown in FIG. 2, may be implemented by one or more computing devices, such as one or more physical servers programmed with associated server code.

Although the inventions have been described in terms of certain preferred embodiments, other embodiments will be apparent to those of ordinary skilled in the art, including embodiments that do not include all of the features and benefits set forth herein. Accordingly, the invention is defined only by the appended claims. Any manner of software designs, architectures or programming languages can be used in order to implement embodiments of the invention. Components of the invention may be implemented in distributed, cloud-based, and/or web-based manners.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

What is claimed is:

1. A method for decision tree based recommendations with improved computer memory performance achieved through minimized memory utilization comprising:
    storing an array of flag bits using single-bit logic to record which textual prompts from a set of possible textual prompts correspond to a first subset of textual prompts, wherein the single-bit logic improves computing efficiency through minimizing the memory utilization for the representation of each textual prompt to a single data bit;
    accessing the array of flag bits to determine the first subset of textual prompts;
    providing, via a user interface, a user device with a series of initial textual prompts from the first subset of textual prompts;
    receiving responses to the series of initial textual prompts, said responses entered into the user interface;
    storing the responses to the series of initial textual prompts;
    determining additional textual prompts, from the set of possible textual prompts, to provide to the user device based upon the responses to the series of initial textual prompts, where predefined relationships between responses and the set of possible textual prompts are used in determining the additional textual prompts;
    providing the user device with the additional textual prompts via the user interface;
    receiving responses to the additional textual prompts;
    storing the responses to the additional textual prompts;
    determining a think-ahead textual prompt to provide to the user device based at least in part on at least one of the received responses to the additional textual prompts, wherein the think-ahead textual prompt is determined without use of predefined relationships between responses and the set of possible textual prompts, and wherein determining the think-ahead textual prompt at a first time provides efficient decisional operation compared to determining the think-ahead textual prompt closer in time to when that query will be provided to the user device, said decisional operation reflected by the fact that the first time for determining the think-ahead textual prompt is closer in time to when the responses to the additional queries, used in making that think-ahead determination, were received;
    providing the user device, via the user interface, with an intervening textual prompt after the think-ahead textual prompt has been determined, the intervening textual prompt different than the think-ahead textual prompt;
    receiving a response to the intervening textual prompt via the user interface, wherein the response to the intervening textual prompt does not affect the previously-made determination to provide the user device with the think-ahead textual prompt;
    storing the response to the intervening textual prompt;
    providing the user device, via the user interface, with the think-ahead textual prompt without requiring, after the providing of the intervening textual prompt, memory retrieval of the responses to the additional textual prompts upon at least one of which the think-ahead textual prompt was based at least in part upon;
    receiving a response to the think-ahead textual prompt via the user interface;
    storing the response to the think-ahead textual prompt;
    determining a recommendation based at least in part on the responses to the series of initial textual prompts, the responses to the additional textual prompts, the response to the intervening textual prompt, and the response to the think-ahead textual prompt;
    generating a natural language note reflecting the responses to the series of initial textual prompts, the responses to the additional textual prompts, the response to the intervening textual prompt, the response to the think-ahead textual prompt, and the recommendation; and providing the natural language note to the user device via the user interface, wherein the method is performed by one or more computer hardware processors.

2. The method of claim 1, further comprising:

accessing lexicographic and grammatical data from a lexicographic data store, said lexicographic data identifying one or more grammatical structures for a natural language including rule sets for the natural language, wherein at least one grammatical structure includes a rule set identifying grammatical relationships between different word types, wherein generating the natural language note uses at least one of the grammatical structures identified in the lexicographic data.

3. The method of claim 1, further comprising:

generating and storing audit trail data, wherein the audit trail data is stored separately from all other data generated by and relied upon by the method, and wherein the audit trail data reflects the received responses from the user device in a manner sufficient to reconstruct the natural language note.

4. The method of claim 1, wherein the user device comprises a tablet computing device.

5. The method of claim 1, further comprising:

storing, on the user device, a copy of the first subset of textual prompts.

6. The method of claim 1, further comprising:

providing, in the user interface, a summary of at least some the responses to the series of initial textual prompts, the responses to the additional textual prompts, the response to the intervening textual prompt, and the response to the think-ahead textual prompt at a predesignated point after receiving some responses.

7. The method of claim 6, further comprising:

receiving, via the user interface, a verification of at least some the responses.

8. The method of claim 6, further comprising:

receiving, via the user interface, edit data for at least some the responses; and storing an updated response based on the edit data.

9. The method of claim 1, further comprising:

receiving, via the user interface, a text description, wherein generating the natural language note further comprises embedding the text description in the natural language note.

10. The method of claim 1, wherein the user interface is displayed in a web browser of the user device.

11. A system for decision tree based recommendations with improved computer memory performance achieved through minimized memory utilization comprising:

a non-transitory computer storage medium configured to at least store an array of flag bits using single-bit logic to record which textual prompts from a set of possible textual prompts correspond to a first subset of textual prompts, wherein the single-bit logic improves computing efficiency through minimizing the memory utilization for the representation of each textual prompt to a single data bit; and one or more computer hardware processors in communication with the non-transitory computer storage medium, the one or more computer hardware processors configured to execute computer-executable instructions to at least:

access the array of flag bits to determine the first subset of textual prompts;

provide a user device with a series of initial textual prompts from the first subset of textual prompts;

receive responses to the series of initial textual prompts;

determine additional textual prompts, from the set of possible textual prompts, to provide the user device based upon the responses, by referencing data for predefined relationships between responses and the set of possible textual prompts;

provide the user device with the additional textual prompts;

receive responses to the additional textual prompts;

determine a think-ahead textual prompt to provide the user device based at least in part on at least one of the received responses to the additional textual prompts, without use of data for predefined relationships between responses and the set of possible textual prompts and wherein the one or more computer hardware processors are further configured to determine the think-ahead textual prompt at a first time to provide efficient decisional operation compared to determining the think-ahead textual prompt closer in time to when that query will be provided to the user device, said decisional operation reflected by the fact that the first time for determining the think-ahead textual prompt is closer in time to when the responses to the additional queries, used in making that think-ahead determination, were received;

provide the user device with an intervening textual prompt after the think-ahead textual prompt has been determined, the intervening textual prompt different than the think-ahead textual prompt;

receive a response to the intervening textual prompt, wherein the response to the intervening textual prompt does not affect the previously-made determination to provide the user device with the think-ahead textual prompt;

provide the user device with the think-ahead textual prompt without requiring, after the providing of the intervening textual prompt, memory retrieval of the responses to the additional textual prompts upon at least one of which the think-ahead textual prompts was based at least in part upon;

receive a response to the think-ahead textual prompt;

determine a recommendation based at least on the responses to the series of initial textual prompts, the responses to the additional textual prompts, the response to the intervening textual prompt, and the response to the think-ahead textual prompt;

generate a natural language note reflecting the responses to the series of initial textual prompts, the responses to the additional textual prompts, the response to the intervening textual prompt, the response to the think-ahead textual prompt, and the recommendation; and provide the natural language note to the user device.

12. The system of claim 11, wherein the one or more computer hardware processors are further configured to:

access lexicographic and grammatical data from a lexicographic data store, said lexicographic data identifying one or more grammatical structures for a natural language including rule sets for the natural language, wherein at least one grammatical structure includes a rule set identifying grammatical relationships between different word types, wherein generating the natural language note uses at least one of the grammatical structures identified in the lexicographic data.

13. The system of claim 11, wherein the one or more computer hardware processors are further configured to:
generate and store audit trail data, wherein the audit trail data is stored separately from all other data generated by and relied upon by the method, and wherein the audit trail data reflects the received responses from the user device in a manner sufficient to reconstruct the natural language note.

14. The system of claim 11, wherein the user device comprises a tablet computing device.

15. The system of claim 11, wherein the one or more computer hardware processors are further configured to:
store, on the user device, a copy of the first subset of textual prompts.

16. The system of claim 11, wherein the one or more computer hardware processors are further configured to:
provide, in the user interface, a summary of at least some the responses to the series of initial textual prompts, the responses to the additional textual prompts, the response to the intervening textual prompt, and the response to the think-ahead textual prompt at a predesignated point after receiving some responses.

17. The system of claim 16, wherein the one or more computer hardware processors are further configured to:
receive, via the user interface, a verification of at least some the responses.

18. The system of claim 16, wherein the one or more computer hardware processors are further configured to:
receive, via the user interface, edit data for at least some the responses; and
store an updated response based on the edit data.

19. The system of claim 11, wherein the one or more computer hardware processors are further configured to:
receive, via the user interface, a text description, wherein to generate the natural language note, the one or more computer hardware processors are further configured to embed the text description in the natural language note.

20. The system of claim 11, wherein a textual prompt comprises a clinical query, and the note comprises clinical data.

* * * * *